(12) United States Patent
Okai

(10) Patent No.: US 10,500,023 B2
(45) Date of Patent: Dec. 10, 2019

(54) REFILL HEAD AND ORAL CARE IMPLEMENT INCLUDING THE SAME

(71) Applicant: COLGATE-PALMOLIVE COMPANY, New York, NY (US)

(72) Inventor: Takahide Okai, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 379 days.

(21) Appl. No.: 15/361,991

(22) Filed: Nov. 28, 2016

(65) Prior Publication Data

US 2017/0151044 A1 Jun. 1, 2017

Related U.S. Application Data

(60) Provisional application No. 62/261,711, filed on Dec. 1, 2015.

(51) Int. Cl.
| | |
|---|---|
| *A46B 5/00* | (2006.01) |
| *A61C 17/22* | (2006.01) |
| *A61C 17/34* | (2006.01) |
| *A46B 9/04* | (2006.01) |

(52) U.S. Cl.
CPC .......... *A61C 17/222* (2013.01); *A46B 5/0095* (2013.01); *A46B 9/04* (2013.01); *A61C 17/3481* (2013.01)

(58) Field of Classification Search
CPC .. A46B 5/0095; A61C 17/222; A61C 17/3481
See application file for complete search history.

(56) References Cited

U.S. PATENT DOCUMENTS

| | | |
|---|---|---|
| 6,766,548 B1 | 7/2004 | Lukas et al. |
| 6,920,659 B2 | 7/2005 | Cacka et al. |
| D517,213 S * | 3/2006 | Vu ................................. D4/104 |

(Continued)

FOREIGN PATENT DOCUMENTS

| | | |
|---|---|---|
| JP | 2009125080 | 6/2009 |
| WO | WO 2013/101300 A1 * | 7/2013 |
| WO | WO2015164486 | 10/2015 |

OTHER PUBLICATIONS

Colgate® 360°® Total® Advanced Floss-Tip† Bristles Toothbrush, http://www.colgatetotal.com/toothbrushes/360-floss-tip, date unknown but downloaded from the Internet prior to the date of the subject application, 3 pp.

(Continued)

*Primary Examiner* — Randall E Chin

(57) ABSTRACT

An oral care implement and a refill head therefor. The refill head may include a sleeve portion and a head portion, a passageway extending through the head portion from a rear surface of the head portion to a front surface of the head portion, a plurality of bristle tufts mounted to the head portion and extending from the front surface of the head portion, and an integrally-formed monolithic mass of an elastomeric material comprising: (1) an elastomeric pad portion located on the rear surface of the head portion; (2) an elastomeric tooth contact element extending from the front surface of the head portion; and (3) an elastomeric anchor portion in the passageway connecting the elastomeric tooth contact element and the elastomeric pad portion.

19 Claims, 13 Drawing Sheets

(56) References Cited

U.S. PATENT DOCUMENTS

| | | |
|---|---|---|
| D632,894 S | 2/2011 | Shigeno et al. |
| D644,439 S | 9/2011 | Shigeno et al. |
| 8,453,285 B2 | 6/2013 | Dickie |
| D696,029 S | 12/2013 | Seyler |
| D702,946 S | 4/2014 | Shigeno et al. |
| 8,800,091 B2 | 8/2014 | Hohlbein |
| 8,800,093 B2 | 12/2014 | Moskovich |
| D724,845 S | 3/2015 | Yoshida et al. |
| D734,613 S | 7/2015 | Yoshida et al. |
| 9,168,117 B2 | 10/2015 | Yoshida et al. |
| 2012/0266397 A1 | 10/2012 | Iwahori |
| 2013/0198980 A1 | 8/2013 | Iwahori et al. |
| 2013/0269128 A1* | 10/2013 | Jimenez ............ A61C 17/3481 15/22.1 |
| 2014/0123414 A1 | 5/2014 | Okazaki |
| 2014/0366289 A1 | 12/2014 | Shimoyama et al. |
| 2016/0000542 A1 | 1/2016 | Yoshida |
| 2018/0296309 A1 | 10/2018 | Yoshida et al. |

OTHER PUBLICATIONS

International Search Report and the Written Opinion of the International Searching Authority issued in International Application PCT/US2016/063830 dated Feb. 28, 2017.

* cited by examiner

REFILL HEAD AND ORAL CARE IMPLEMENT INCLUDING THE SAME

CROSS-REFERENCE TO RELATED PATENT APPLICATIONS

This application claims the benefit of priority to U.S. Provisional Patent Application Ser. No. 62/261,711 filed Dec. 1, 2015, the entirety of which is incorporated herein by reference.

BACKGROUND

An oral care implement, such as a toothbrush, is used to clean the teeth by removing plaque and debris from the tooth surfaces. Toothbrushes have a handle for gripping and a head which is inserted into a user's mouth for tooth and oral surface cleaning. Powered or electric toothbrushes exist that include a handle component that contains all of the electronic components of the toothbrush and a refill head that is detachably coupled to the handle component. In the past, substantial research and development has gone into technological improvements for imparting vibrational, rotary, and translational movement to the tooth cleaning elements of powered toothbrushes to improve the performance of such toothbrushes. However, there has been very little development directed towards improving the comfort and performance of the refill head and the tooth cleaning elements thereon. Thus, a need exists for an oral care implement and refill head therefor that addresses the above-noted needs.

BRIEF SUMMARY

The present invention may be directed, in one aspect, to a refill head for an electric toothbrush handle and to an oral care implement that includes a handle component and a refill head. The refill head may be detachably coupled to the handle component of the oral care implement. The refill head may include a sleeve portion and a head portion having a front surface and a rear surface. A plurality of bristle tufts may be mounted to the head portion and extend from the front surface of the head portion. Furthermore, an integrally formed monolithic mass of elastomeric material may be coupled to the head portion. The integrally formed monolithic mass of elastomeric material may include one or more of the following: an elastomeric pad on the rear surface of the head; a plurality of protrusions extending from a rear surface of the pad; an elastomeric tooth cleaning extending from the front surface of the head; and an elastomeric anchor portion in the passageway.

In one aspect, the invention may be an oral care implement comprising a handle component comprising: a gripping section extending from a proximal end to a distal end; a stem extending from the distal end of the gripping section, the stem comprising a stem cavity and terminating in a sealed distal end; a power source; and a vibratory source disposed in the stem cavity and operably coupled to the power source; a refill head comprising: a sleeve portion having a sleeve cavity extending along a longitudinal axis from a blind top end to an open bottom end located at a proximal end of the sleeve portion; a head portion located at a distal end of the sleeve portion, the head portion and the sleeve portion formed of a rigid material; a passageway extending through the head portion from a rear surface of the head portion to a front surface of the head portion; a plurality of bristle tufts mounted to the head portion and extending from the front surface of the head portion; and an integrally formed monolithic mass of an elastomeric material comprising: (1) an elastomeric pad portion located on the rear surface of the head portion; (2) an elastomeric tooth contact element extending from the front surface of the head portion; and (3) an elastomeric anchor portion in the passageway connecting the elastomeric tooth contact element and the elastomeric pad portion; and the refill head alterable between: (1) a decoupled state in which the refill head is separated from the handle component; and (2) a coupled state in which the stem of the handle component is disposed within the sleeve cavity of the refill head such that vibrational energy generated by the vibratory source imparts vibrational movement to the bristle tufts, and the elastomeric tooth contact element.

In another aspect, the invention may be a refill head for an electric toothbrush handle, the refill head comprising: a sleeve portion having a sleeve cavity extending along a longitudinal axis from a blind top end to an open bottom end located at a proximal end of the sleeve portion; a head portion located at a distal end of the sleeve portion, the head portion and the sleeve portion formed of a rigid material; a passageway extending through the head portion from a rear surface of the head portion to a front surface of the head portion; a plurality of bristle tufts mounted to the head portion and extending from the front surface of the head portion; and an integrally formed monolithic mass of an elastomeric material comprising: (1) an elastomeric pad portion located on the rear surface of the head portion; (2) an elastomeric tooth contact element extending from the front surface of the head portion; and (3) an elastomeric anchor portion in the passageway connecting the elastomeric tooth contact element and the elastomeric pad portion.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
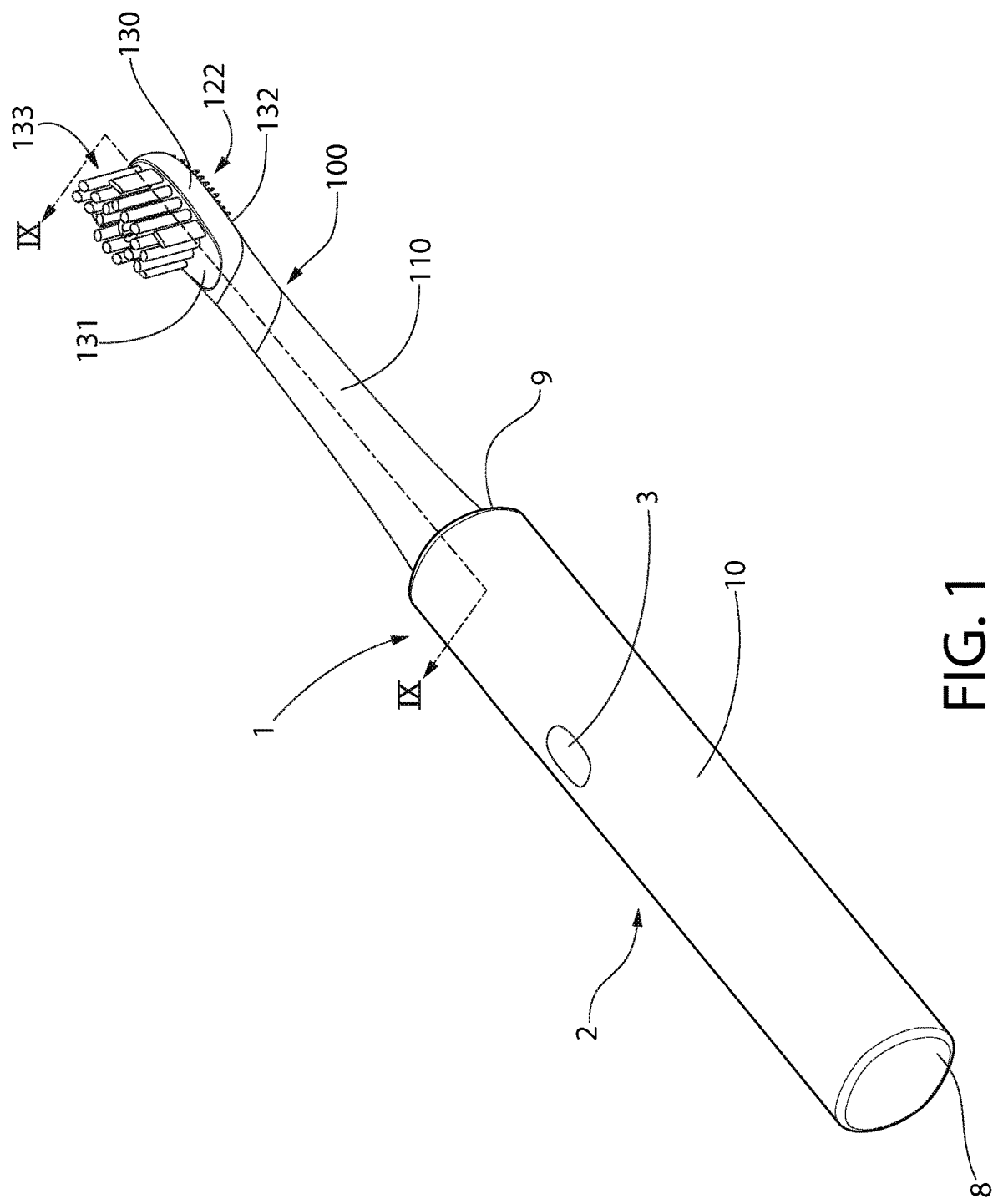
FIG. 1 is perspective view of an oral care implement having a handle component and a refill head in accordance with an embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Figure 2:
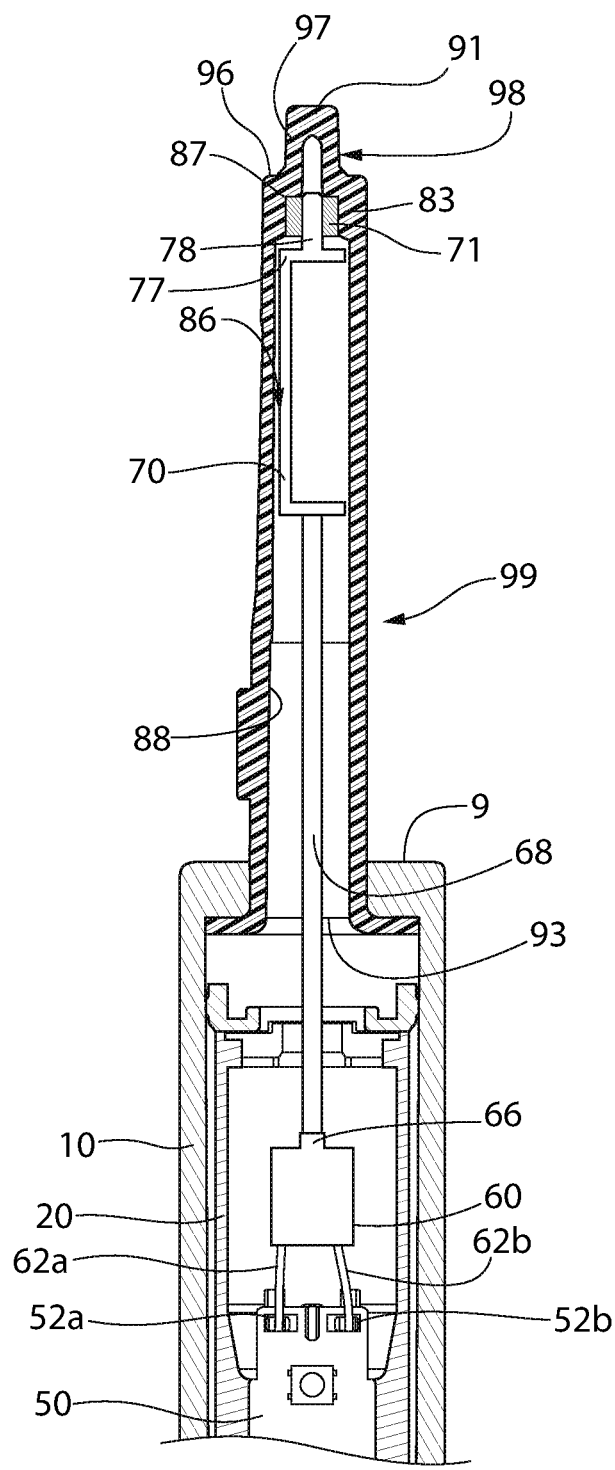
FIG. 2 is a cross-sectional view of a portion of a gripping section and a stem of the handle component of the oral care implement of FIG. 1.
Figure 3:
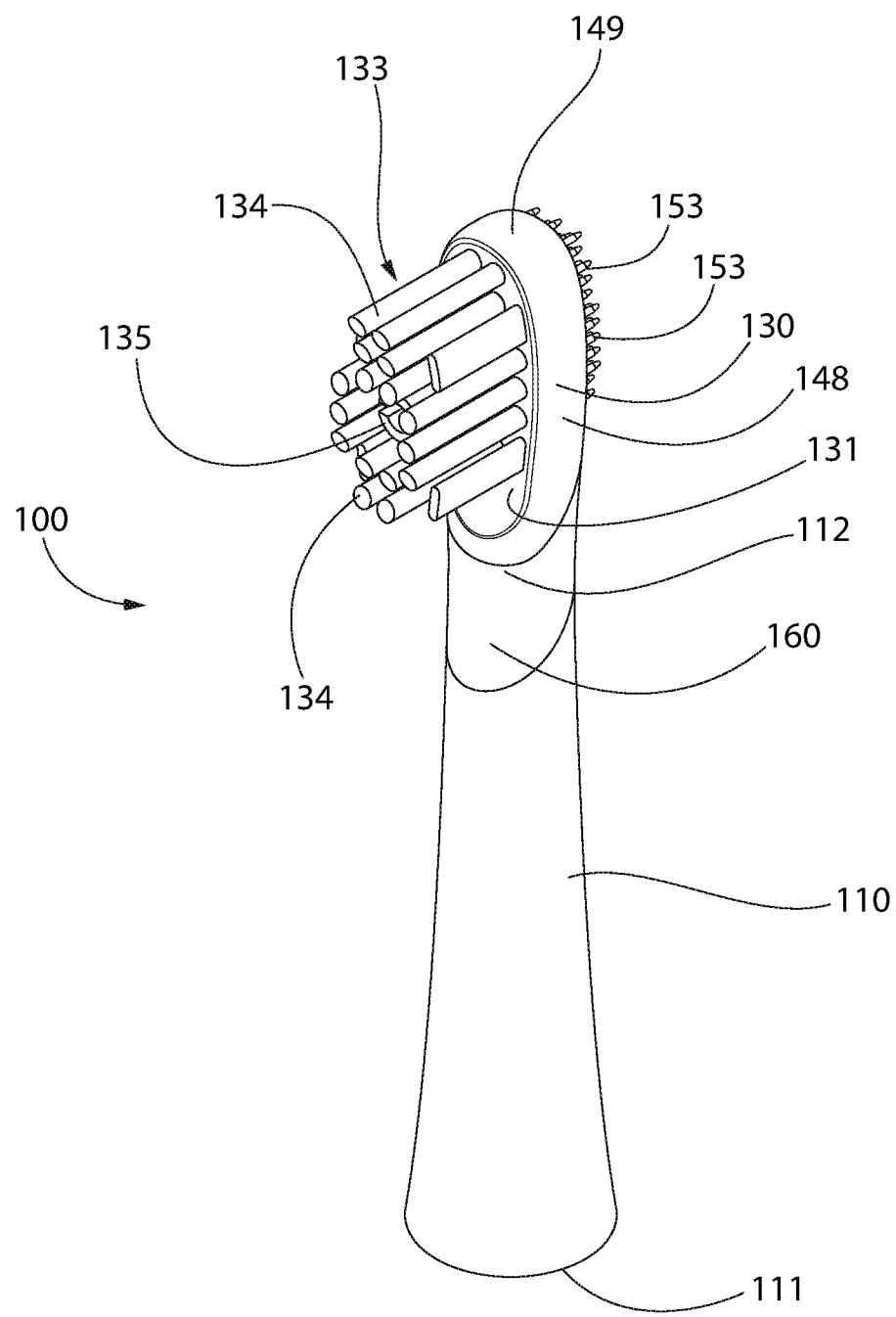
FIG. 3 is a front perspective view of the refill head of FIG. 3.
Figure 4:
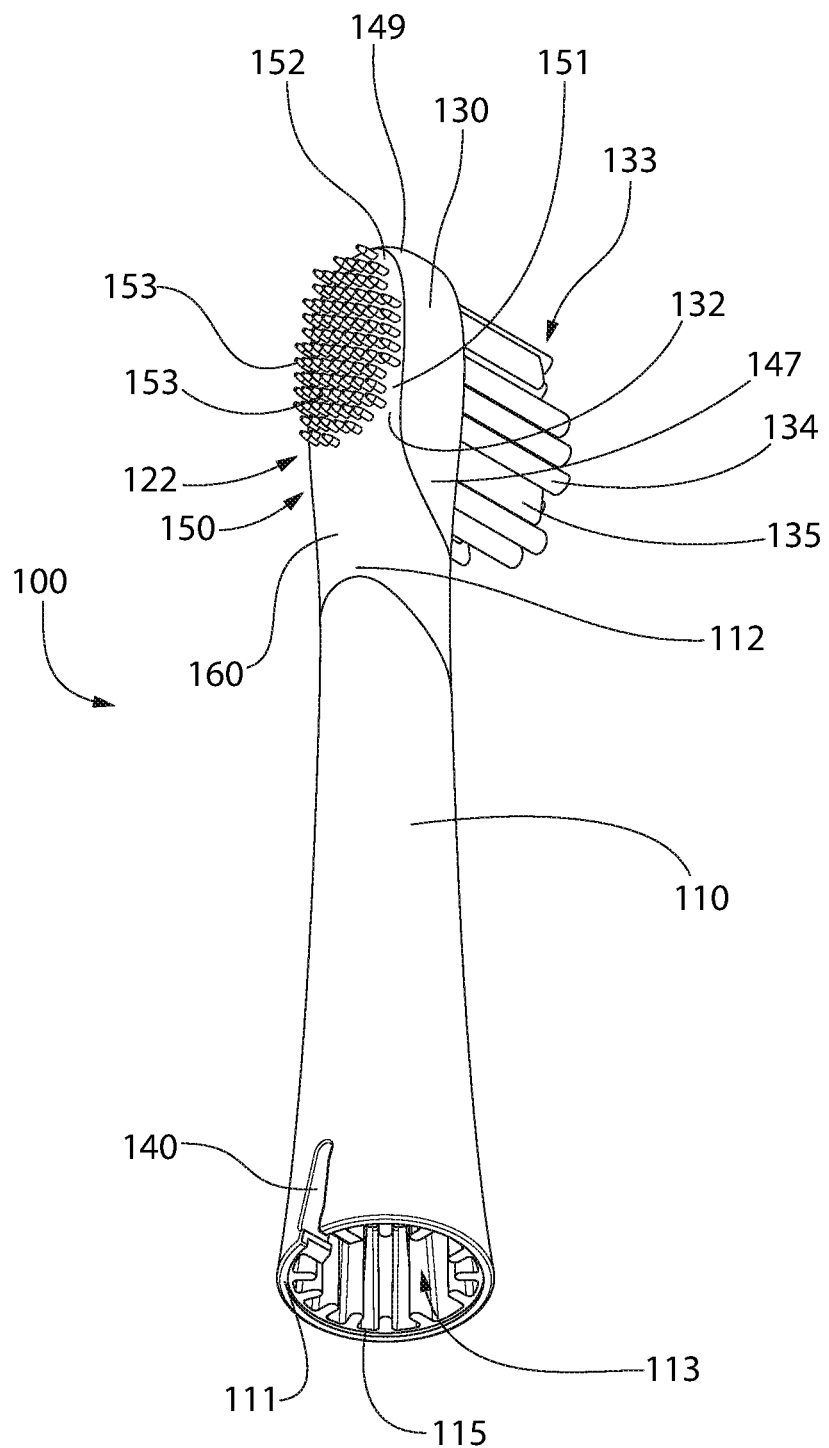
FIG. 4 is a rear perspective view of the refill head of FIG. 3.

Referring to FIGS. 1 and 2 concurrently, an oral care implement 1 will be described in accordance with an embodiment of the present application. In the exemplified embodiment, the oral care implement 1 is an electric or powered toothbrush. However, the invention is not to be so limited in all embodiments. In certain other embodiments the device may be a manual toothbrush having a replaceable head portion. Thus, the invention is not to be limited to an electric or powered oral care implement 1 in all embodiments unless explicitly claimed as such.

The oral care implement 1 generally comprises a handle component 2 and a refill head 100. The handle component 2 comprises a gripping section 10 extending from a proximal end 8 to a distal end 9 and a stem 83 extending from the distal end 9 of the gripping section 10. In the exemplified embodiment the gripping section 10 of the handle component 2 comprises an actuator 3, such as a button, that facilitates powering the oral care implement 1 on and off when the oral care implement 1 is a powered or electric toothbrush. Of course, the actuator 3 can be positioned at other locations on the handle component 2 than that which is shown in the drawings in other embodiments. The refill head 100 is detachably coupled to the stem 83 of the oral care implement 1 as described herein below. Different variations of refill heads may be used with and coupled to/decoupled from the handle component 2 so that a user has options regarding the type of refill head desired for use.

The refill head 100 generally comprises a sleeve portion 110 and a head portion 130. The sleeve portion 110 of the refill head 100 slides over the stem 83 of the handle component 2 to couple the refill head 100 to the stem 83. A plurality of tooth cleaning elements 133 are mounted to the head portion 130 and extend from a front surface 131 of the head portion 130 of the refill head 100. A soft tissue cleaner 122 formed of an elastomeric material is coupled to or mounted on a rear surface 132 of the head portion 130 of the refill head 100. The details of one embodiment of the refill head 100 will be described in detail below with reference to FIGS. 3-8. The details of an alternative refill head 200 will be described in detail below with reference to FIGS. 10-13.

The handle component 2 of the oral care implement 1 includes the gripping section 10, a chassis 20, a power source (although not illustrated, the power source may be a rechargeable battery, a non-rechargeable battery, battery cells, printed batteries, super capacitors, a control circuit that stores electrical energy, or the like), a circuit board 50, a motor 60 (which may have a cylindrical body as illustrated) having a drive shaft 66, a vibratory source 70, and a spindle 68 operably coupling the drive shaft 66 of the motor 60 to the vibratory source 70. The gripping section 10 is capable of being gripped or grasped by a user to enable the user to manipulate the oral care implement 1 during use. The gripping section 10 also houses the electronic circuitry and components necessary for operation of the oral care implement 1 as a powered or electric toothbrush. In certain embodiments, the power source may be omitted and the device may be powered by a plug that is coupled to a power supply, such as a wall socket. The gripping section 10 of the handle component 2 has an interior cavity for accommodating the chassis 20, the power source, and the circuit board 50. The interior cavity of the gripping section 10 may be cylindrical in some embodiments although the invention is not to be so limited in all embodiments.

The stem 83 comprises a cavity 86 for receiving and/or retaining the vibratory source 70 in certain embodiments. The vibratory source 70 may be positioned at other locations within the handle component 2 in other embodiments. The motor 60 in the exemplified embodiment is positioned within the gripping section 10 of the handle component 2, but it may be positioned within the stem 83 in other embodiments. The stem 83 has an open bottom end 93 that provides a passageway into the cavity 86 and the stem 83 terminates in a sealed distal end 91.

The bottom of the vibratory source 70 may be formed with a recess or protrusion configured to to be engaged with the spindle 68 and/or the drive shaft 66 of the motor 60 so that the motor 60 can rotate the vibratory source 70 to impart a desired movement to the refill head 100. The motor 60 has two wires 62a and 62b extending from a bottom face thereof for electric connection with the circuit board 50 and operable coupling to the power source. The vibratory source 70 includes an eccentric portion 77 and an axial shaft portion 78.

As noted above, the motor 60 is operably coupled to the power source. The drive shaft 66 of the motor 60 is operably coupled to the eccentric portion 77 of the vibratory source 70 (either directly or via the spindle 68) to rotate the eccentric portion 77 and cause vibrations in the refill head 100, or specifically to the head portion 130 or the tooth cleaning elements 133 thereon. Specifically, when the vibratory source 70 rotates about its axis by the motor 60, the eccentric portion 77 generates a high frequency vibration which is transmitted to the stem 83 and to the refill head 100 coupled thereto.

The stem 83 generally comprises a body portion 99 that comprises the cavity 86 and an engagement portion 98 at the distal end 91 of the stem 83. The engagement portion 98 of the stem 83 engages an inner surface of the sleeve portion 110 of the refill head 100 when the refill head 100 is coupled to the handle component 2, as discussed in more detail below with specific reference to FIG. 9. The engagement portion 98 of the stem 83 comprises a stem tip 97 extending from an upper surface 96 of the body portion 99 of the stem 83. The upper surface 96 of the body portion 99 of the stem 83 forms an annular transverse shoulder that surrounds the stem tip 97.

In the exemplified embodiment, the cavity 86 accommodates therein the vibratory source 70, and it may also accommodate the motor 60 although this is not the case in the exemplified embodiment. A recess 87 may be formed at the end of the cavity 86 adjacent the distal end 91 of the stem 83. The recess 87 may slidably receive the axial shaft portion 78 of the vibratory source 70. Thus, an upper end of the eccentric portion 77 of the vibratory source 70, which includes the axial shaft portion 78, may be mounted within or adjacent to the stem tip 97. Thus, in the exemplified embodiment the eccentric portion 77 of the vibratory device 70 is rotatably mounted within the cavity 86. The vibratory source 70 is operably coupled to the power source via the necessary electrical components such as wires or the like. The recess 87 may serve as a bearing for freely holding the axial shaft portion 78 of the vibratory source 70. The vibratory source 70 may be freely rotated in the cavity 86 even under high frequency vibration. In certain embodiments, because the recess 87 serves as the bearing, it is not necessary to provide a separate bearing arrangement for rotatably holding the axial shaft portion 78. Of course, a separate bearing assembly, such as an annular bearing 71, may be provided in some embodiments.

As noted above, the cavity 86 has an open bottom end 93 at the lower end of the stem 83. The two wires 62a and 62b of the motor 60 extend through the open bottom end 93 of the cavity 86, through an opening formed in the chassis 20, and terminate at electrodes 52a and 52b formed on the circuit board 50. The cavity 86 has an interior wall 88 that may have a constant cross-sectional area or may taper in some embodiments.

In certain embodiments, the stem 83 and the gripping section 10 may be formed integrally. In this case a bottom end of the gripping section 10 should be opened to allow the insertion of an assembly of the vibratory source 70, motor 60, and chassis 20 mounted with the power source and circuit board 50. After the assembly is inserted from the bottom open end, the open end should be tightly closed by a cap member.

Referring to FIGS. 3-8 concurrently, one embodiment of the refill head 100 that can be detachably coupled to the handle component 10, and specifically to the stem 83, of the oral care implement 1 will be described. As discussed above, the refill head 100 generally comprises the sleeve portion 110 that is coupled directly to the stem 83 and the head portion 130. In certain embodiments, the head portion 130 and the sleeve portion 110 are formed of a rigid material, such as a rigid plastic material including without limitation polymers and copolymers of ethylene, propylene, butadiene, vinyl compounds and polyesters such as polyethylene terephthalate. The head portion 130 and the sleeve portion 110 may be integrally formed or separately formed and later coupled together. In the exemplified embodiment the head and sleeve portion 130, 110 are integrally formed in an injection molding process.

The sleeve portion 110 extends from a proximal end 111 to a distal end 112. The sleeve portion 110 comprises a sleeve cavity 113 that extends along a longitudinal axis A-A from a blind top end 114 to an open bottom end 115 that is located at the proximal end 111 of the sleeve portion 110. The blind top end 114 of the sleeve cavity 113 is blind because it is not visible from the exterior of the refill head 100. The sleeve cavity 113 accommodates the stem 83 of the handle component 2 to permit coupling of the refill head 100 to the handle component 2 as described herein and discussed in particular with reference to FIG. 9.

The sleeve cavity 113 comprises an entry section 171 and an engagement section 172. The entry section 171 of the sleeve cavity 113 has a first minimum diameter and comprises the open bottom end 115 of the sleeve cavity 113. The engagement section 172 of the sleeve cavity 113 has a second minimum diameter that is less than the first minimum diameter. In certain embodiments the maximum diameter of the engagement section 172 is less than the minimum diameter of the entry section 171.

The sleeve portion 110 comprises an outer surface 119 and an inner surface 173, the inner surface 173 defining the sleeve cavity 113. The inner surface 173 of the sleeve portion 110 comprises an annular transverse shoulder 174 located between the entry section 171 of the sleeve cavity 113 and the engagement section 172 of the sleeve cavity 113. The sleeve cavity 113 further comprises an uppermost section 175 located between the engagement section 172 and the blind top end 114 of the sleeve cavity 113. In the exemplified embodiment, the uppermost section 175 of the sleeve cavity 113 has a transverse cross-sectional area that continually decreases with distance from the engagement section 172 of the sleeve cavity 113 towards the blind top end 114 of the sleeve cavity 113.

The refill head 100 comprises a coupling element 140 located near the proximal end 111 of the sleeve portion 110. In this embodiment, the coupling element 140 is an opening formed into the sleeve portion 110 that extends from the open bottom end 115 of the sleeve portion 110 upwardly in the direction of the head portion 130 for a portion of the length of the refill head 100. The coupling element 140 may have a specific structure or shape that permits the coupling element 140 to mate with a coupling element on the stem 83 to facilitate coupling and/or locking the refill head 100 to the stem 83.

The head portion 130 of the refill head 100 is located at the distal end 112 of the sleeve portion 110 and comprises a front surface 131 and an opposing rear surface 132. As discussed above, there are a plurality of tooth cleaning elements 133 extending from the front surface 131 of the head portion 130 of the refill head 100. The plurality of tooth cleaning elements 133 comprise a plurality of bristle tufts 134 that are mounted to the head portion 130 and extend from the front surface 131 of the head portion 130. Each of the bristle tufts 134 may comprise a plurality of bristles. The bristles may be filament bristles, fiber bristles, spiral bristles, nylon bristles, or the like. Each of the above-referenced types of bristles may be end-rounded or tapered. The bristle tufts 134 may be coupled to the head portion 130 using staple technology, anchor-free tufting technologies, or the like as desired.

Figure 7:
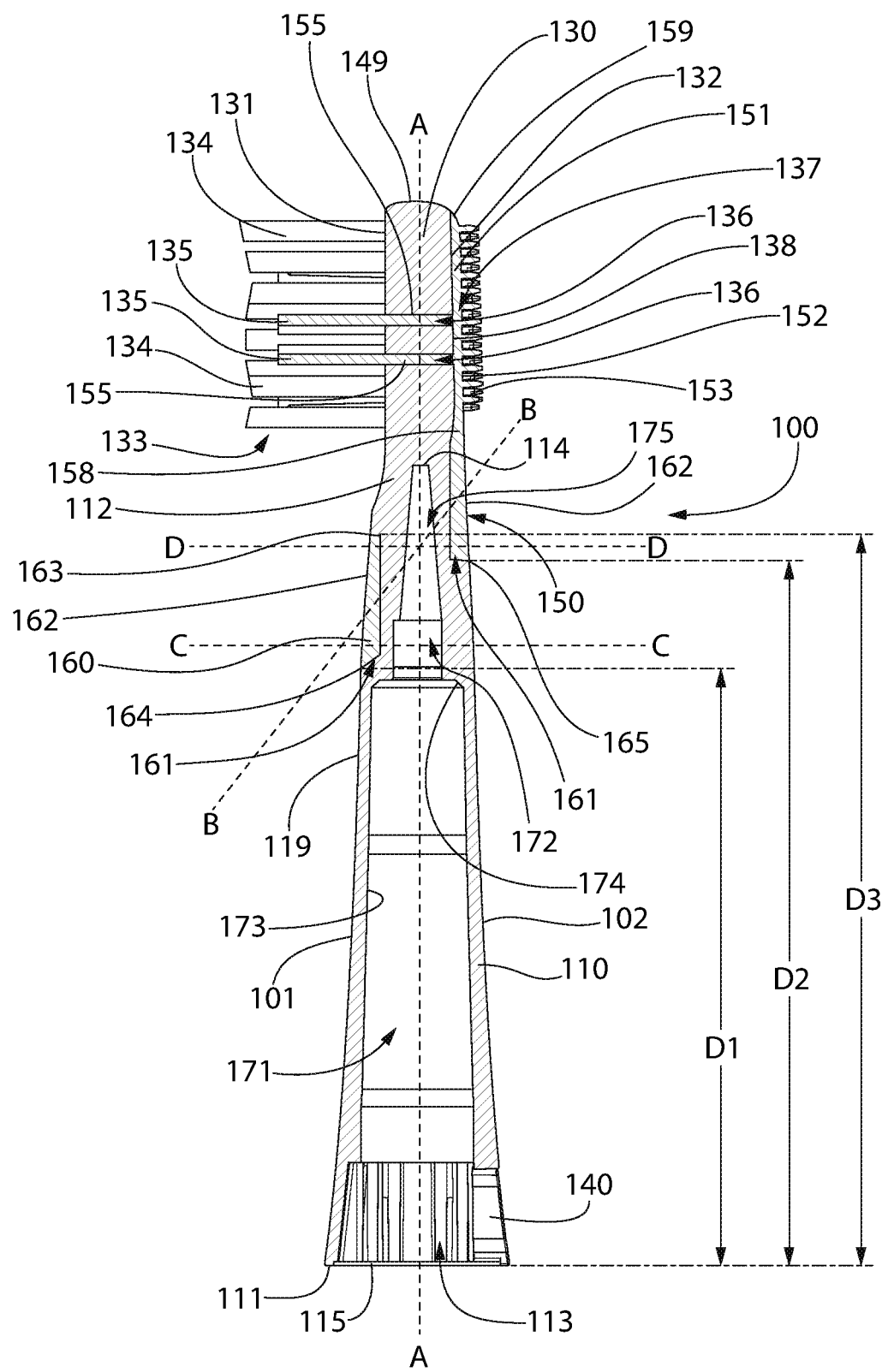
FIG. 7 is a cross-sectional view taken along line VII-VII of FIG. 6.
Figure 8:
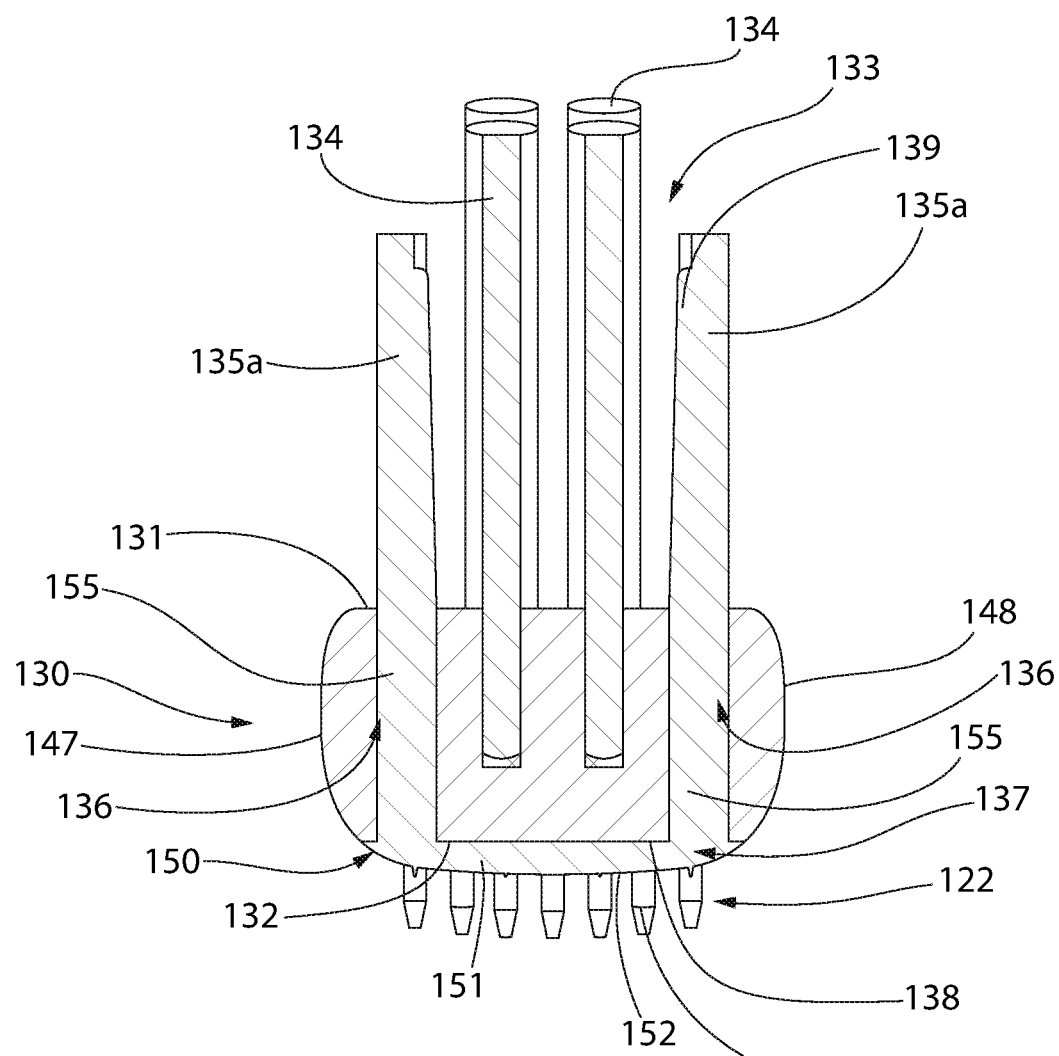
FIG. 8 is a cross-sectional view taken along line VIII-VIII of FIG. 6.

In addition to the bristle tufts 134, the tooth cleaning elements 133 may include one or more elastomeric tooth contact elements 135 extending from the front surface 131 of the head portion 130. In certain embodiments the bristle tufts 134 form a bristle field, and the elastomeric tooth contact elements 135 are located within the bristle field. In the exemplified embodiment, as best illustrated in FIGS. 7 and 8, the bristle tufts 134 extend to a height above the front surface 131 of the head portion 130 of the refill head 100 that is greater than a height that the elastomeric tooth contact elements 135 extend above the front surface 131 of the head portion 130 of the refill head 100.

In the exemplified embodiment, the bristle tufts 134 and the elastomeric tooth contact elements 135 has a specific pattern on the head portion 130 of the refill head 100. However, this is merely one exemplary embodiment and other patterns for the bristle tufts 134 and the elastomeric tooth cleaning contact 135 are possible, including that which will be described below with reference to FIGS. 10-13.

In this embodiment, the elastomeric tooth contact elements 135 include four peripheral contact elements 135a and two central contact elements 135b. The peripheral contact elements 135a include two peripheral contact elements 135a that are transversely aligned near a proximal end of the head portion 130 and two peripheral contact elements 135a that are transversely aligned near a distal end of the head portion 130. The peripheral contact elements 135 are linear wall-like segments having a rib 139 protruding from its inner surface. Thus, the ribs 139 of the peripheral contact elements 135 face inwardly towards a center of the head portion 130.

The two central contact elements 135b are arcuate shaped contact elements positioned centrally on the head portion 130 of the refill head 100. The central contact elements 135b are arranged to form a loop having gaps that are aligned along a plane that extends transverse to the longitudinal axis A-A. The central contact elements 135b have concave surfaces that face one another and convex surfaces facing away from one another and towards the proximal and distal ends of the head portion 130 of the refill head 100, respectively.

The bristle tufts 134 include three peripheral bristle tufts on each opposing side of the head, the three peripheral bristle tufts being positioned between two of the peripheral contact elements 135a in the longitudinal direction of the head portion 130 of the refill head 100. The bristle tufts also include four proximal bristle tufts located between the bottom one of the central contact elements 135b and the proximal end of the head portion 130 and six distal bristle tufts located between the top one of the central contact elements 135b and the distal end of the head portion 130. The four proximal tufts are positioned generally between two of the peripheral contact elements 135a located near the proximal end of the head portion 130. The six distal proximal tufts are positioned generally between two of the peripheral contact elements 135a located near the distal end of the head portion 130.

As discussed herein, the elastomeric tooth contact elements 135 are formed as an integral part of a monolithic mass of elastomeric material 150, as discussed below. In certain embodiments the monolithic mass of elastomeric material 150 may be a formed from thermoplastic elastomer, although the invention is not to be so limited in all embodiments and it may be another type of resilient material or rubber in other embodiments.

In the exemplified embodiment, there are one or more passageways 136 extending through the head portion 130 from the front surface 131 of the head portion 130 to the rear surface 132 of the head portion 130. Furthermore, the integrally formed monolithic mass of elastomeric material 150 is coupled to the head portion 130. Specifically, the monolithic mass of elastomeric material 150 comprises an elastomeric pad portion 151 located on the rear surface 132 of the head portion 130, elastomeric protuberances 153 extending from the pad portion 151, the elastomeric tooth contact elements 135, and an elastomeric anchor portion 155 in the passageways 136 connecting the elastomeric tooth contact elements 135 to the pad portion 151.

In the exemplified embodiment, a basin 137 is formed into the rear surface 132 of the head portion 130. The basin 137 is a recess or depression having a floor 138. The elastomeric pad portion 151 of the integrally formed monolithic mass of elastomeric material 150 is positioned within the basin 137 and in contact with the floor 138. The elastomeric pad portion 151 comprises a rear surface 152 that forms at least a portion of the rear surface 132 of the head portion 130 of the refill head 100. The monolithic mass of elastomeric material 150 comprises a plurality of the elastomeric protuberances 153 extending from the rear surface 152 of the elastomeric pad portion 151 of the monolithic mass of elastomeric material 150. The elastomeric pad portion 151 and the elastomeric protuberances 153 extending therefrom for the soft tissue cleaner 122 as discussed above.

The one or more passageways 136 are positioned within the basin 137 formed into the rear surface 132 of the head portion 130. Specifically, the one or more passageways 136 terminate at an opening in the floor 138 of the basin 137 and an opening in the front surface 131 of the head portion 130. Thus, the monolithic mass of elastomeric material 150 can pass through the passageways 136 to simultaneously form the elastomeric pad portion 151, the elastomeric anchor portion 155, and the elastomeric tooth contact elements 135. In that regard, as described above the monolithic mass of elastomeric material 150 comprises one or more of the elastomeric tooth contact elements 135 extending from the front surface 131 of the head portion 130 and one or more of the elastomeric anchor portions 155 positioned within the passageways 136 and connecting the elastomeric tooth contact elements 135 to the elastomeric pad portion 151.

In certain embodiments, the integrally formed monolithic mass of elastomeric material 150 may be formed in a single shot injection molding process. Thus, the head portion 130 of the refill head 100 may be positioned within a mold cavity, and then an elastomeric material may be injected onto the head portion 130 of the refill head 100 within the mold cavity. The elastomeric material will simultaneously form the elastomeric pad portion 151, the elastomeric protuberances 153, the elastomeric tooth contact elements 135, and the elastomeric anchor portions 155.

In addition to the above, the monolithic mass of elastomeric material 150 also comprises an elastomeric ring portion 160 that circumscribes the sleeve portion 110 of the refill head 100. Thus, the elastomeric ring portion 160 may be integrally formed with the elastomeric pad portion 151, the elastomeric protuberances 153, the elastomeric tooth contact elements 135, and the elastomeric anchor portions 155. In the exemplified embodiment, the elastomeric ring portion 160 extends around the entire circumference of the sleeve portion 110. The elastomeric pad portion 151 extends from a proximal end 158 to a distal end 159 that is adjacent to the distal end of the head portion 130 of the refill head 100. The elastomeric ring portion 160 is connected to and extends from the proximal end 158 of the elastomeric pad portion 151.

The sleeve portion 110 of the refill head 100 comprises the outer surface 119 that includes a front surface 101 and an opposing rear surface 102. The elastomeric ring portion 160 nests within an annular depression 161 that is formed into the outer surface 119 of the sleeve portion 110 of the refill head 100. The elastomeric ring portion 160 has an outer surface 162 that is substantially flush with the outer surface 119 of the sleeve portion 110 of the refill head 100. Thus, the elastomeric ring portion 160 does not protrude from the outer surface 119 of the sleeve portion 110 of the refill head 100 but rather forms a smooth, continuous outer surface of the refill head 100 along with the outer surface 119 of the sleeve portion 110. When viewed from the front surface 131 of the head portion 130 of the refill head 100, the elastomeric ring portion 160 has a concave top edge 163 and a convex bottom edge 164. When viewed from the rear surface 132 of the head portion 130 of the refill head 100, the elastomeric ring portion 160 has a concave bottom edge 165. When viewed from the rear surface 132, the top edge of the the elastomeric ring portion 160 flows continuously into the elastomeric pad portion 151.

The head portion 130 of the refill head 100 comprises a peripheral edge 146 extending between the front and rear surfaces 131, 312 of the refill head 100. The peripheral edge 146 includes opposing first and second lateral edges 147, 148 and a distal edge 149. In the exemplified embodiment, the entirety of the peripheral edge 146 of the head portion 130 of the refill head 100 is devoid of the monolithic mass of elastomeric material 150 or any other elastomeric material. Thus, the rigid material of the refill head 100 is exposed along the entire peripheral edge 146 of the head portion 130 of the refill head 100.

Figure 5:
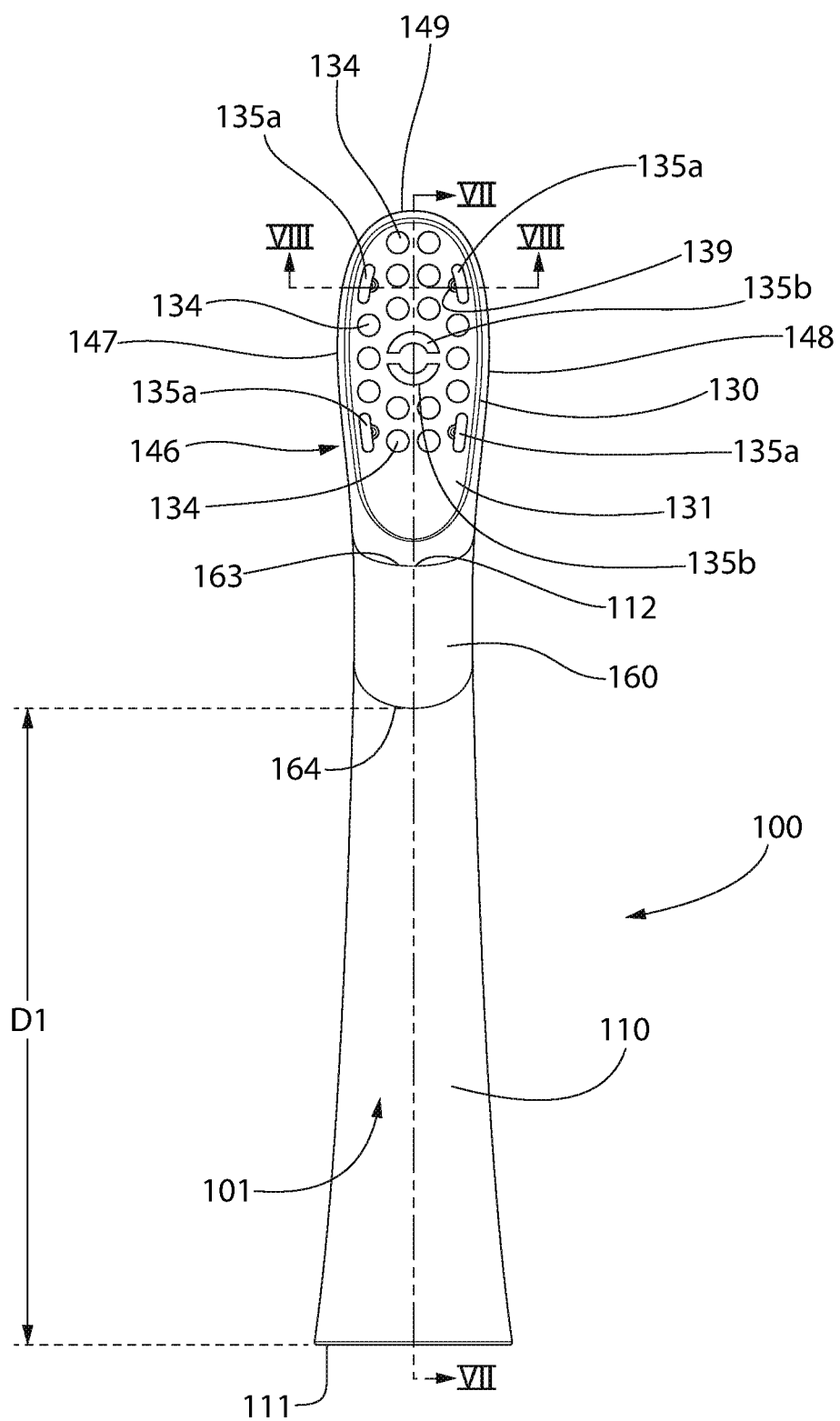
FIG. 5 is a front view of the refill head of FIG. 3.
Figure 6:
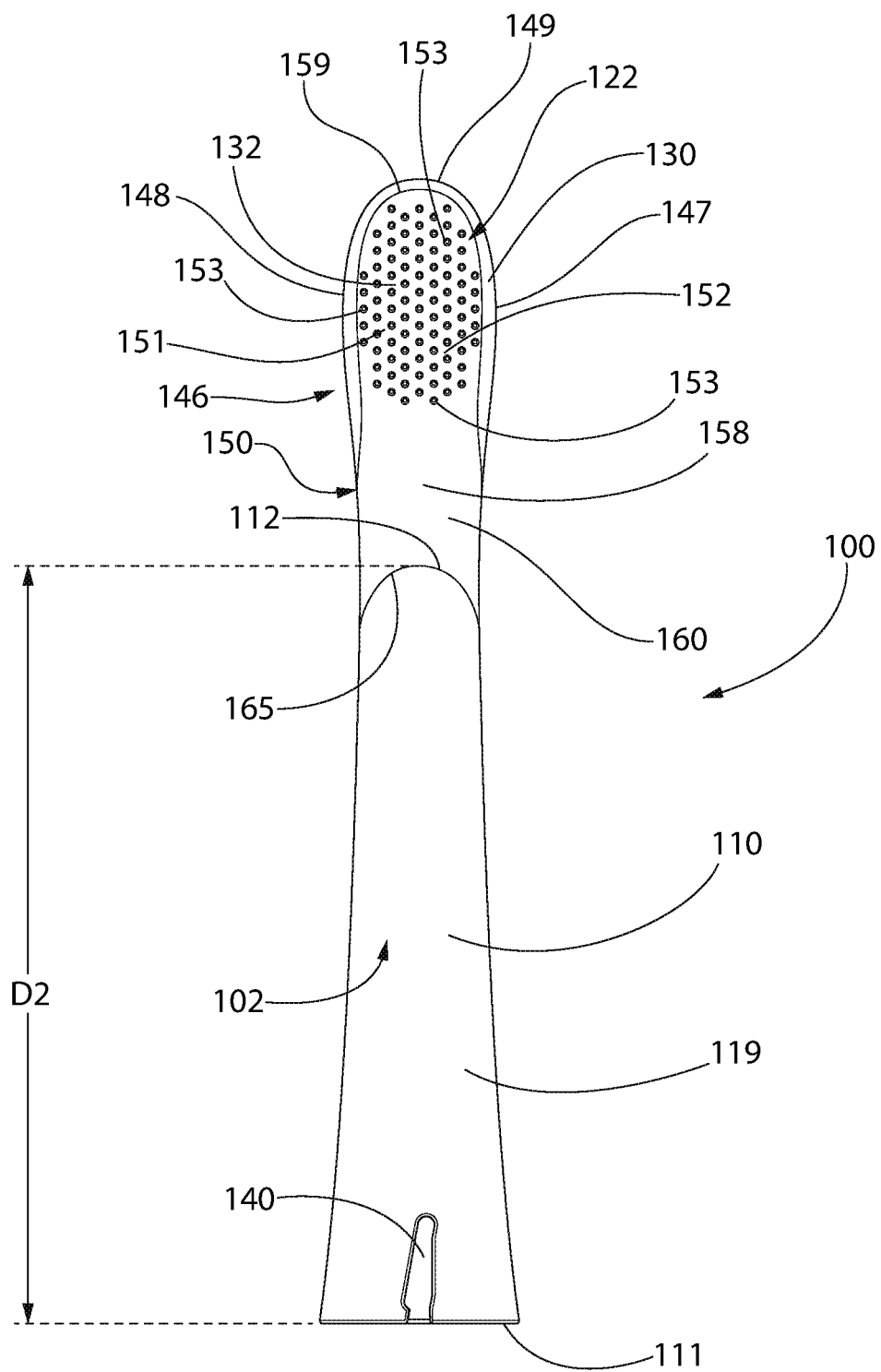
FIG. 6 is a rear view of the refill head of FIG. 3.

To get a full appreciation of the shape and orientation of the elastomeric ring portion 160, FIGS. 5-7 must be viewed concurrently. The elastomeric ring portion 160 is positioned such that an annular centerline B-B of the elastomeric ring portion 160 is oriented oblique to the longitudinal axis A-A of the sleeve cavity 113. This oblique orientation is achieved in part due to the different spacing of the bottom portions of the elastomeric ring portion 160 from the proximal end 111 of the sleeve portion 110 of the refill head 100 on the front and rear surfaces 101, 102 of the refill head 110. Specifically, the convex bottom edge 164 of the elastomeric ring portion 160 on the front surface 101 of the sleeve portion 110 of the refill head 100 is spaced a first distance D1 from the proximal end 111 of the sleeve portion 110 of the refill head 100. The convex bottom edge 165 of the elastomeric ring portion 160 on the rear surface 102 of the sleeve portion 110 of the refill head 100 is spaced a second distance D2 from the proximal end 111 of the sleeve portion 110 of the refill head 100. The second distance D2 is greater than the first distance D1. Furthermore, the concave top edge 163 of the elastomeric ring portion 160 on the front surface 101 of the sleeve portion 110 of the refill head 100 is spaced a third distance D3 from the proximal end 111 of the sleeve portion 110 of the refill head 100, the third distance D3 being greater than each of the first and second distances D1, D2. There exists a transverse plane, such as plane D-D, which extends perpendicular to the longitudinal axis A-A and that intersects a portion of the elastomeric ring portion 160 on both of the front and rear surfaces 101, 102 of the sleeve portion 110 of the refill head 100.

The thickness of the elastomeric ring portion 160 of the monolithic mass of elastomeric material 150 is generally thicker than the thickness of the elastomeric pad portion 151 of the monolithic mass of elastomeric material. Specifically, the elastomeric ring portion 160 has a maximum thickness that is greater than a maximum thickness of the elastomeric pad portion 151. In certain embodiments, the elastomeric ring portion 160 may have a minimum thickness that is greater than a maximum thickness of the elastomeric pad portion 151. This provides the potential for greater flexibility of the head portion 130 of the refill head 100 relative to the sleeve portion 110 of the refill head 100 about the elastomeric ring portion 160.

The elastomeric ring portion 160 of the monolithic mass of elastomeric material 150 is transversely aligned with the engagement section 172 of the sleeve cavity 113. Thus, a transverse plane C-C that is perpendicular to the longitudinal axis A-A of the sleeve cavity 113 intersects both the engagement section 172 of the sleeve cavity 113 and the elastomeric ring portion 160.

Figure 9:
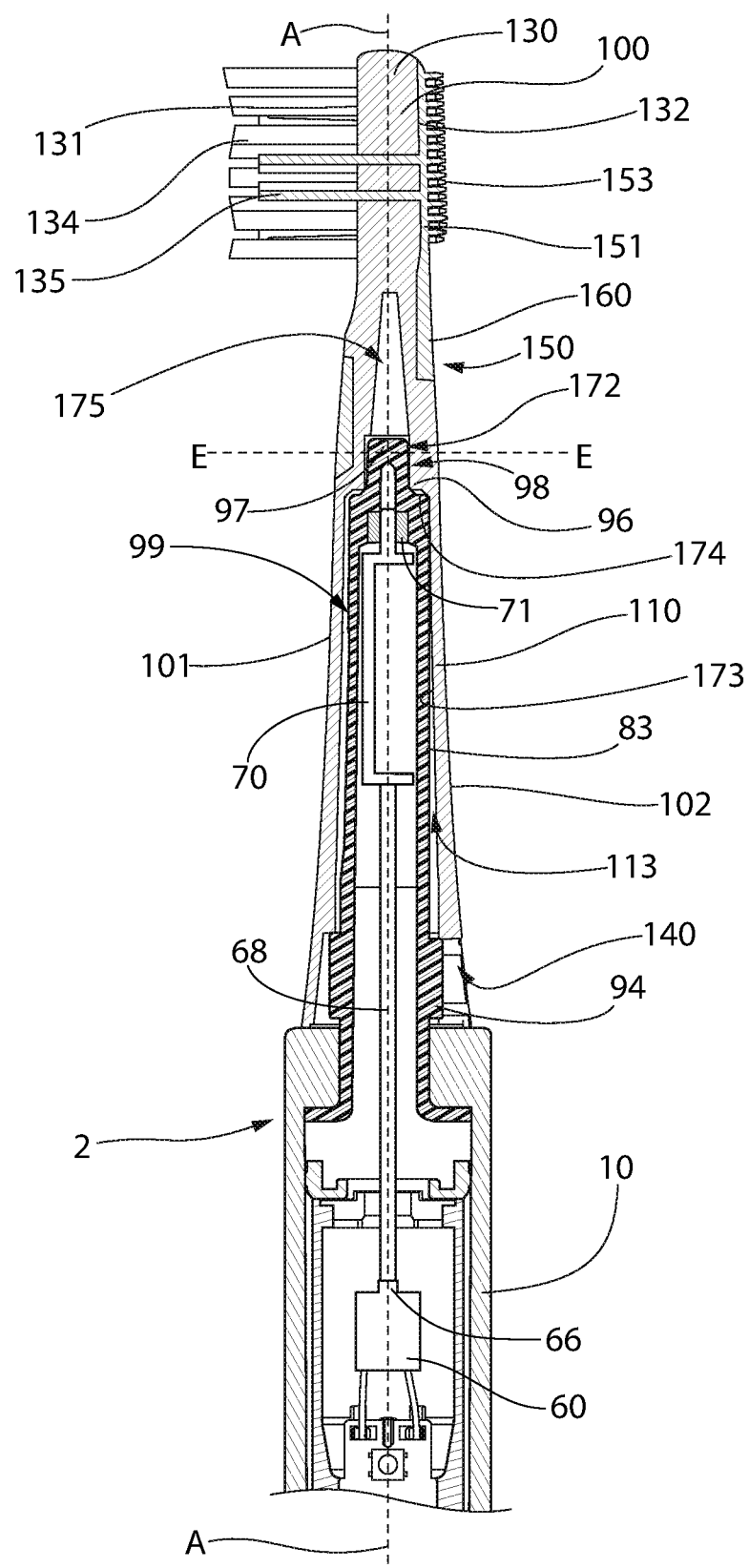
FIG. 9 is a cross-sectional taken along line IX-IX of FIG. 1.
Figure 10:
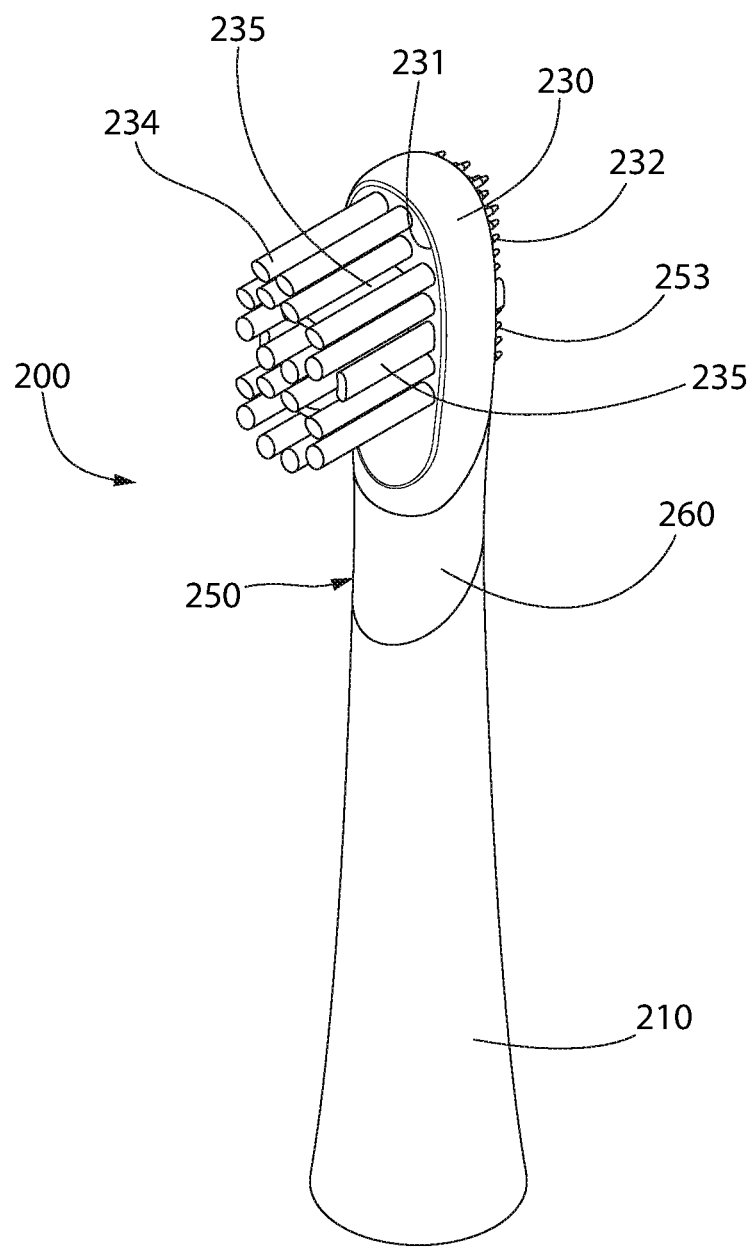
FIG. 10 is a front perspective view of a refill head in accordance with an alternative embodiment of the present invention.
Figure 11:
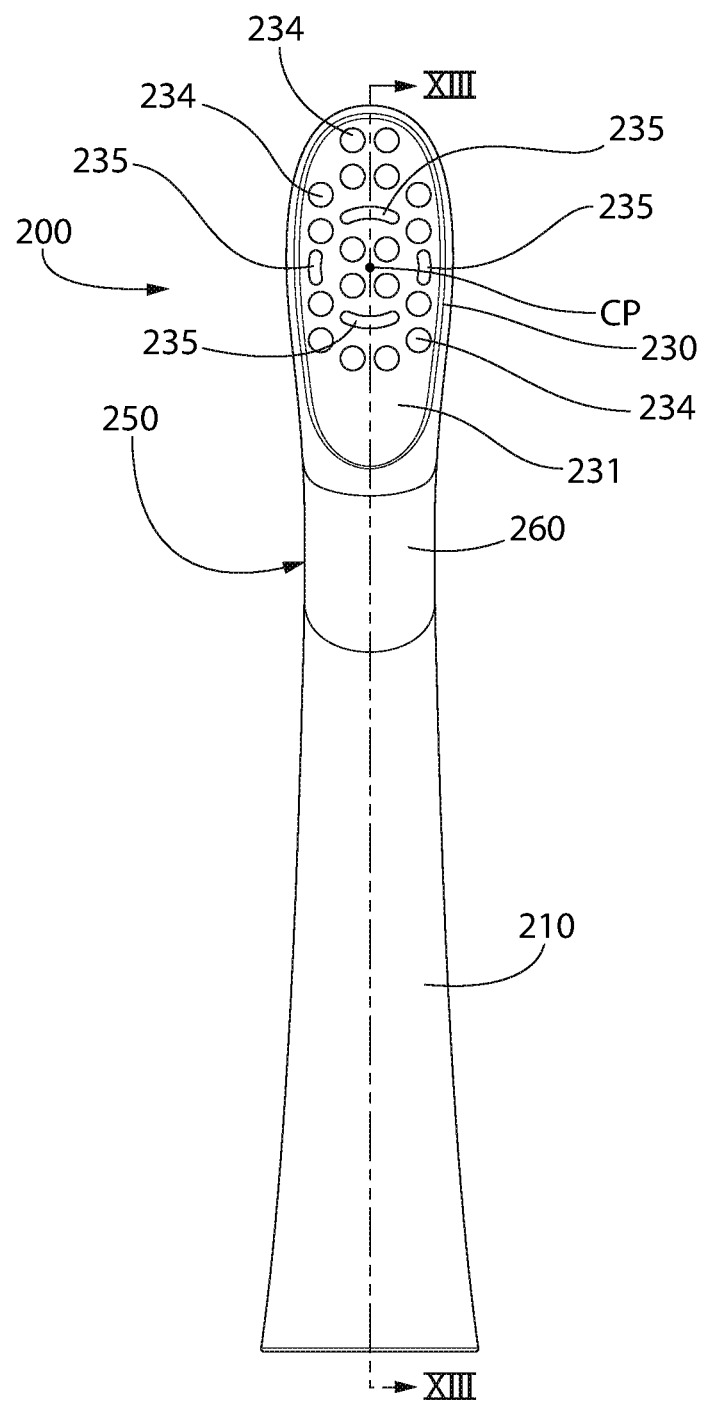
FIG. 11 is a front view of the refill head of FIG. 10.
Figure 12:
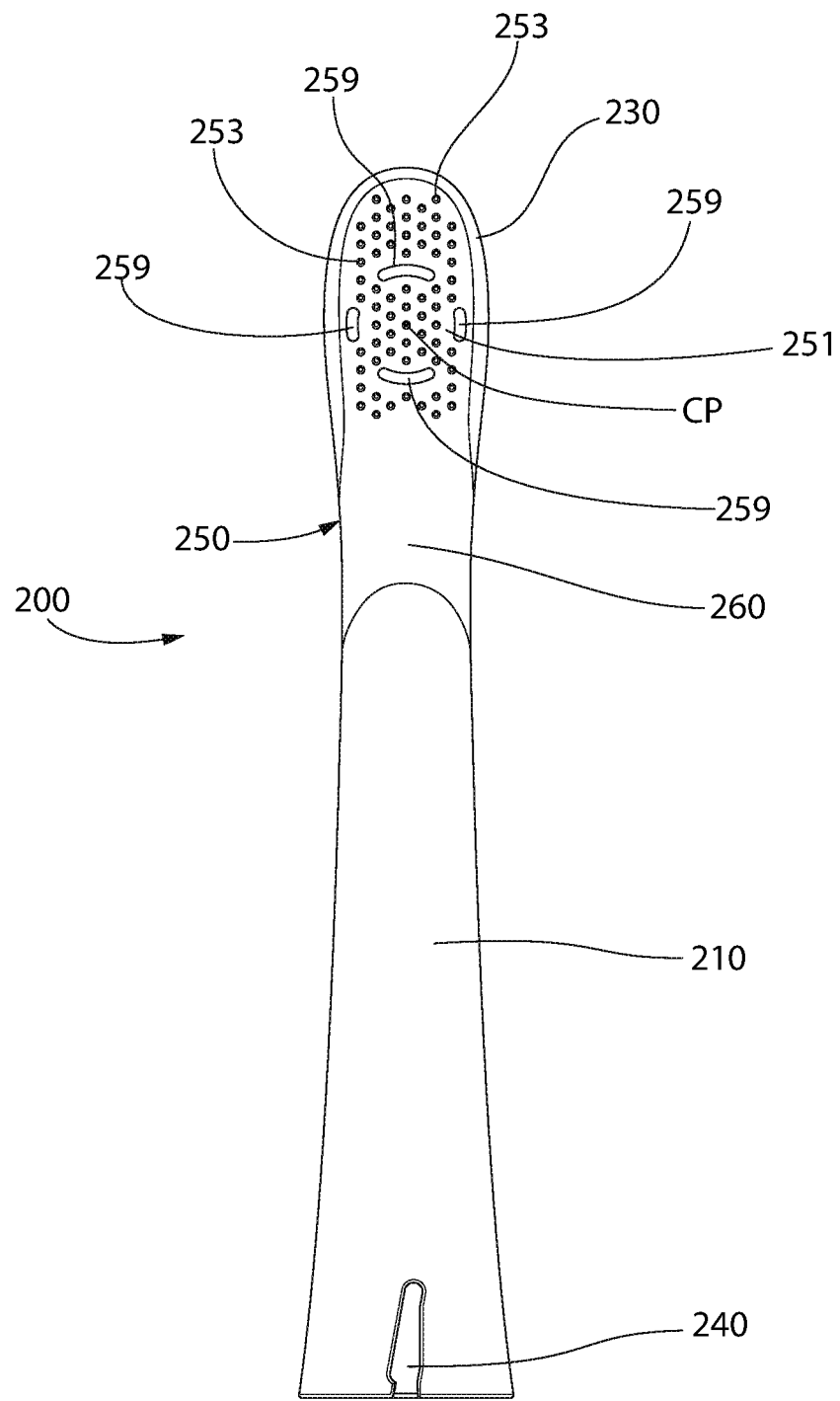
FIG. 12 is a rear view of the refill head of FIG. 10.
Figure 13:
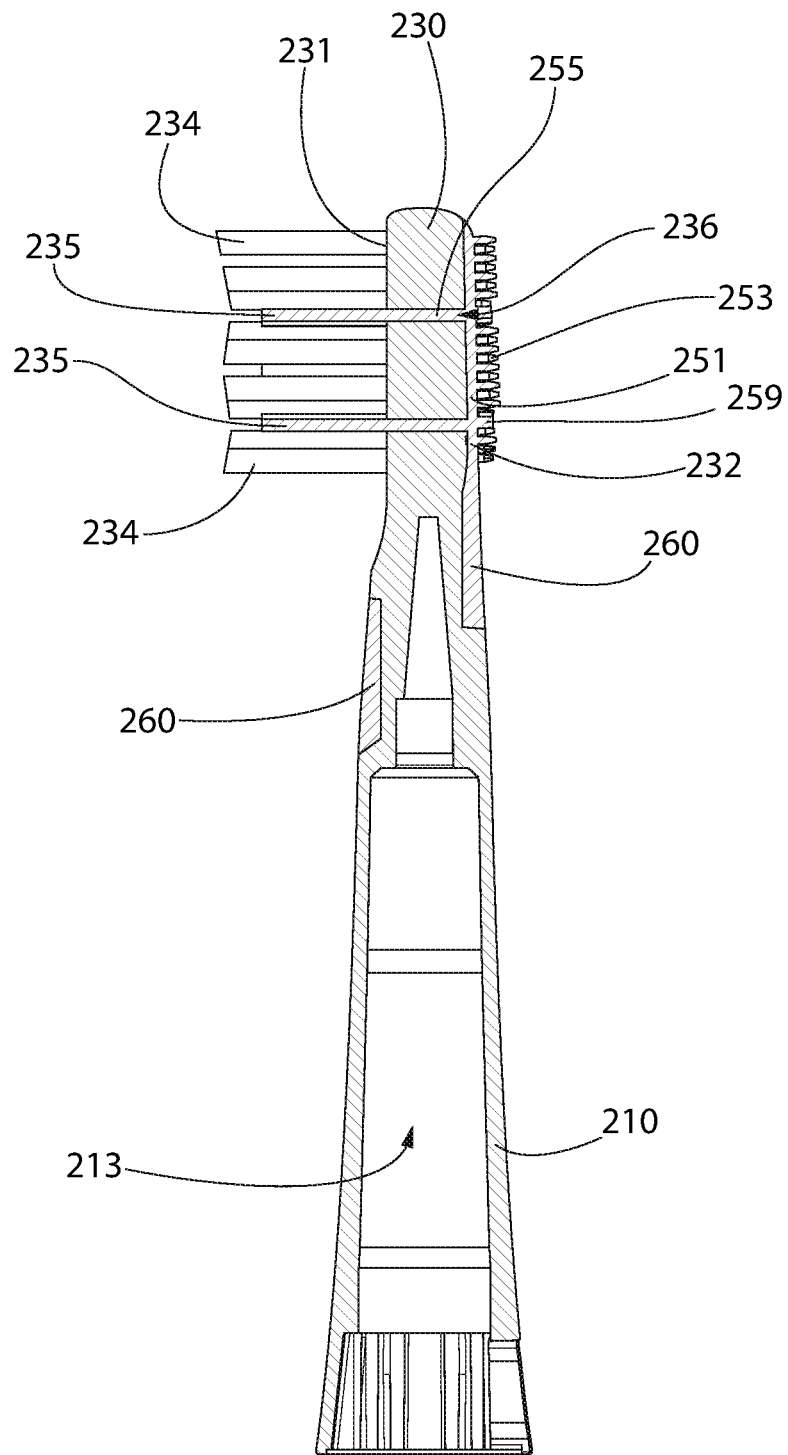
FIG. 13 is a cross-sectional view taken alone line XIII-XIII of FIG. 11.

Referring to FIG. 9, a cross-sectional view of a portion of the oral care implement 1 is illustrated with the refill head 100 coupled to the stem 83. As discussed above, the refill head 100 may be detachably coupled to the handle component 2, and particularly to the stem 83. Thus, the refill head 100 can be used and replaced when the tooth cleaning elements 134, 135 are worn out while the handle component 2 and all of the circuitry can continue to be reused with the new refill head. Different refill heads with different tooth cleaning element constructions and patterns may be used with the same handle component 2 as desired to achieve different cleaning effects and performances.

The refill head 100 is alterable between a coupled state, as illustrated in FIGS. 1 and 9, in which the stem 83 of the handle component 2 is disposed within the sleeve cavity 113 of the refill head 100 and a decoupled state (not illustrated) in which the refill head 100 is separated from the handle component 2. In the coupled state, vibrational energy generated by the vibratory source 70 imparts vibrational movement to the bristle tufts 134, the elastomeric tooth contact elements 135, and the elastomeric protuberances 153.

With continued reference to FIG. 9, the structural cooperation between the components of the refill head 100 and the components of the handle component 2 and stem 83 will be described with the refill head 100 in the coupled state. During coupling of the refill head 100 to the handle component 2, the stem 83 is inserted into the sleeve cavity 113 of the refill head 100 until the upper surface 96 of the body portion 99 of the stem 83 contacts the annular transverse shoulder 174 of the inner surface 173 of the sleeve portion 110 of the refill head 100 that defines the sleeve cavity 113. In this position, the body portion 99 of the stem 83 is positioned within the entry section 171 of the sleeve cavity 113 and the the stem tip 97 extends into the engagement section 172 of the sleeve cavity 113. Furthermore, in certain embodiments in the coupled state the engagement portion 98 at the distal end of the stem 83 engages the inner surface 173 of the sleeve portion 110 of the refill head 100.

The stem 83 includes a coupling element 94 that cooperates with the coupling element 140 of the refill head 100. Specifically, the coupling element 94 of the stem 83 is a protuberance that has a size and shape that permits mating cooperation with the coupling element 140 opening so that as the stem 83 is inserted into the sleeve cavity 113, the coupling element 94 of the stem 83 enters into the coupling element 140 of the refill head 100. The mating cooperation between the coupling element 94 of the stem 83 and the coupling element 140 of the refill head 100 facilitates locking the refill head 100 to the handle component 2 in the coupled state. Specifically, the refill head 100 remains coupled to the handle component 2 until the refill head 100 and the handle component 2 are pulled in opposite directions in the direction of the longitudinal axis A-A with sufficient force to overcome the locking engagement between the coupling elements 94, 140 of the stem 83 and the refill head 100.

When the refill head 100 is coupled to the handle component 2, the sleeve portion 110 of the refill head 100 circumferentially surrounds the stem 83 of the handle component 2 and the head portion 110 of the refill head 100 extends from the stem 83 of the handle component 2. Furthermore, the stem 83 does not fill the entirety of the sleeve cavity 113. Specifically, in the coupled state the uppermost section 175 of the sleeve cavity 113 remains empty and free of the stem 83. Furthermore, in the coupled state the engagement portion 98 of the stem 83 and the elastomeric ring portion 160 of the monolithic mass of elastomeric material 150 are transversely aligned. Thus, a transverse plane E-E that is perpendicular to the longitudinal axis A-A of the sleeve cavity 113 intersects both the engagement portion 98 of the stem 83 and the elastomeric ring portion 160 of the monolithic mass of elastomeric material 150. In the exemplified embodiment, the engagement portion 98 of the stem 83 is aligned with a portion of the elastomeric ring portion 160 on the front surface 101 of the sleeve portion 110 of the refill head 100 but is not also aligned with a portion of the elastomeric ring portion 160 on the rear surface 102 of the sleeve portion 110 of the refill head 100. Thus, in the exemplified embodiment there is no transverse plane perpendicular to the longitudinal axis A-A that intersects the stem 83 and the elastomeric ring portion 160 located on the rear surface 102 of the sleeve portion 110 of the refill head 100. The elastomeric ring portion 160 is transversely aligned with the uppermost section 175 of the sleeve cavity 113, which is empty as noted above. This further enhances potential flexibility of the head portion 130 of the refill head 100 relative to the sleeve portion 110 of the refill head 100 about the region of the refill head 100 that includes the elastomeric ring portion 160 due to a decrease in the thickness of the rigid material in that region.

Referring to FIGS. 10-13, an alternative refill head 200 that can be coupled to the handle component 2 of the oral care implement 1 will be described. Most of the structure of the refill head 200 is the same as the structure of the refill head 100 described above, and thus it will not be repeated herein in the interest of brevity. Rather, it should be understood that the description of the refill head 100 applies to the refill head 200 except as discussed herein below. The refill head 200 will be similarly numbered to the refill head 100 except that the 200-series of numbers will be used. It should be understood that for features of the refill head 200 that are similarly numbered to features of the refill head 100, the description of that feature with regard to the refill head 100 is also applicable to the refill head 200 unless stated otherwise herein below. For features of the refill head 200 that are numbered but not described, the description of the refill head 100 above applies.

The refill head 200 generally comprises a sleeve portion 210 defining a sleeve cavity 213 and a head portion 230 having a front surface 231 and an opposite rear surface 232. Tooth cleaning elements, such as bristle tufts 234, extend from the front surface 231 of the head portion 230. An integral monolithic mass of elastomeric material 250 is coupled to the refill head 200 and includes an elastomeric pad portion 251 located on the rear surface 232 of the head portion 230, elastomeric protuberances 253, 259 extending from the rear surface of the pad portion 251, elastomeric anchor portions 255 in passageways 236 that extend through the head portion 230, and elastomeric tooth contact elements 235 extending from the front surface 231 of the head portion 230. The monolithic mass of elastomeric material 250 may also include an elastomeric ring portion 260 similar to the elastomeric ring portion 150 described above with regard to the refill head 100.

The main difference between the refill head 200 and the refill head 100 is in the pattern of the bristle tufts 234 and the elastomeric tooth contact elements 235 and the structure of the protuberances 259 extending from the elastomeric pad portion 251 of the monolithic mass of elastomeric material 250. Specifically, in this embodiment there are four elastomeric tooth contact elements 235 that are arranged in a loop about a centerpoint CP of the head portion 230. Each of the elastomeric tooth contact elements 235 is arcuate shaped having a concave surface facing the centerpoint CP and a convex surface facing away from the centerpoint CP. The elastomeric tooth contact elements 235 are equidistantly spaced from the centerpoint CP. There are four bristle tufts 234 positioned within the loop formed by the four elastomeric tooth contact elements 235. In certain embodiments, the four bristle tufts 234 may extend a height from the front surface 231 of the head portion 230 of the refill head 200 that is greater than a height that the elastomeric tooth contact elements 235 extend from the front surface 231 of the head portion 230 of the refill head 200. In certain embodiments, every bristle tuft 234 extends a height from the front surface 231 of the head portion 230 of the refill head 200 that is greater than the height that the elastomeric tooth contact elements 235 extend from the front surface 231 of the head portion 230 of the refill head 200.

The elastomeric tooth contact elements 235 are coupled to the elastomeric pad portion 251 via the anchor portions 255 that extend through the passageways 236 in the head portion 230. Furthermore, the protuberances 259 that are aligned with the elastomeric tooth contact elements 235 have a shape that coincides with the shape of the elastomeric tooth contact elements 235 with which it is aligned. Thus, there are four protuberances 259 arranged in a loop about the centerpoint CP. The four protuberances 259 have the same size, shape, and location as the four elastomeric tooth contact elements 235 with which they are aligned except that the four protuberances 259 extend from the rear surface 232 of the head portion 230 of the refill head 200 and the four elastomeric tooth contact elements 235 extend from the front surface 231 of the head portion 230 of the refill head 200. Thus, the four protuberances 259 are arcuate shaped having inner concave surfaces that face the centerpoint CP and outer convex surfaces that face away from the centerpoint CP. The remainder of the protuberances 253 are nub-like protrusions having a conical or cylindrical shape.

In certain embodiments, the tooth contact elements 235, the passageways 236, the anchor portions 255, and the protuberances 259 all have an identical shape. This gives the appearance that the tooth contact elements 235 extend through the head portion 230 and protrude from both the front and rear surfaces 231, 232 of the head portion 230 of the refill head 200.

In addition to the four bristle tufts 234 positioned within the loop, there are two bristle tufts 234 positioned above and below the elastomeric tooth contact elements 235 on the peripheral sides of the front surface 231 of the head portion 230, four bristle tufts 234 positioned in a square-like pattern between the upper-most elastomeric tooth contact element 235 and a distal end of the head portion 230, and two bristle tufts 234 positioned between the lower-most elastomeric tooth contact element 235 and a proximal end of the head portion 230. The upper-most and lower-most elastomeric tooth contact elements 235 are substantially surrounded by a grouping of the bristle tufts 234, and specifically by eight separate bristle tufts 234. The elastomeric tooth contact elements 235 on the peripheral sides of the front surface 231 of the head portion 230 are bounded by a grouping of the bristle tufts 234 (i.e., four of the bristle tufts 234) and by the lateral sides of the head portion 230.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care implement comprising:
    a handle component comprising:
        a gripping section extending from a proximal end to a distal end;
        a stem extending from the distal end of the gripping section, the stem comprising a stem cavity and terminating in a sealed distal end;
        a power source; and
        a vibratory source disposed in the stem cavity and operably coupled to the power source;
    a refill head comprising:
        a sleeve portion having a sleeve cavity extending along a longitudinal axis from a blind top end to an open bottom end located at a proximal end of the sleeve portion;
        a head portion located at a distal end of the sleeve portion, the head portion and the sleeve portion formed of a rigid material;
        a passageway extending through the head portion from a rear surface of the head portion to a front surface of the head portion;
        a plurality of bristle tufts mounted to the head portion and extending from the front surface of the head portion; and
        an integrally-formed monolithic mass of an elastomeric material comprising: (1) an elastomeric pad portion located on the rear surface of the head portion and comprising a plurality of elastomeric protuberances extending from the elastomeric pad portion; (2) an elastomeric tooth contact element extending from the front surface of the head portion; and (3) an elastomeric anchor portion in the passageway connecting the elastomeric tooth contact element and the elastomeric pad portion;
    and
        the refill head alterable between: (1) a decoupled state in which the refill head is separated from
    the handle component; and (2) a coupled state in which the stem of the handle component is disposed within the sleeve cavity of the refill head such that vibrational energy generated by the vibratory source imparts vibrational movement to the bristle tufts and the elastomeric tooth contact element.

2. The oral care implement according to claim 1 wherein in the coupled state, vibrational energy generated by the vibratory source imparts vibrational movement to the plurality of elastomeric protuberances.

3. The oral care implement according to claim 1 wherein the integrally formed monolithic mass of elastomeric material further comprises an elastomeric ring portion that circumscribes the sleeve portion.

4. The oral care implement according to claim 3 wherein the elastomeric ring portion is connected to a proximal end of the elastomeric pad portion.

5. The oral care implement according to claim 4 wherein an annular centerline of the elastomeric ring portion is oblique to the longitudinal axis of the sleeve cavity.

6. The oral care implement according to claim 3 wherein the elastomeric ring portion nests within an annular depression formed in an outer surface of the sleeve portion, an outer surface of the elastomeric ring portion being substantially flush with the outer surface of the sleeve portion.

7. The oral care implement according to claim 3 further comprising:
    the stem comprising:
        a body portion comprising the stem cavity; and
        an engagement portion at a distal end of the stem that engages an inner surface of the sleeve portion of the refill head;
    and
    wherein in the coupled state, the engagement portion and the elastomeric ring portion are transversely aligned so that a transverse plane that is perpendicular to the longitudinal axis of the sleeve cavity intersects both the engagement portion of the stem and the elastomeric ring portion of the refill head.

8. The oral care implement according to claim 3 wherein the elastomeric ring portion has a maximum thickness that is greater than a maximum thickness of the elastomeric pad portion.

9. The oral care implement according to claim 1 wherein the bristle tufts form a bristle field, the elastomeric tooth contact element located within the bristle field.

10. The oral care implement according to claim 1 further comprising:
    the refill head comprising a plurality of the passageways; and
    the monolithic mass of the elastomeric material comprising a plurality of the elastomeric tooth contact elements and a plurality of the elastomeric anchor portions.

11. A refill head for an electric toothbrush handle, the refill head comprising:
    a sleeve portion having a sleeve cavity extending along a longitudinal axis from a blind top end to an open bottom end located at a proximal end of the sleeve portion;
    a head portion located at a distal end of the sleeve portion, the head portion and the sleeve portion formed of a rigid material;
    a passageway extending through the head portion from a rear surface of the head portion to a front surface of the head portion;
    a plurality of bristle tufts mounted to the head portion and extending from the front surface of the head portion; and
    an integrally-formed monolithic mass of an elastomeric material comprising: (1) an elastomeric pad portion located on the rear surface of the head portion and comprising a plurality of elastomeric protuberances extending from a rear surface of the pad portion; (2) an elastomeric tooth contact element extending from the front surface of the head portion; and (3) an elastomeric anchor portion in the passageway connecting the elastomeric tooth contact element and the elastomeric pad portion.

12. The refill head according to claim 11 wherein the integrally-formed monolithic mass of elastomeric material further comprises an elastomeric ring portion that circumscribes the sleeve portion.

13. The refill head according to claim 12 wherein the elastomeric ring portion is connected to a proximal end of the elastomeric pad portion, and wherein an annular centerline of the elastomeric ring portion is oblique to the longitudinal axis of the sleeve cavity.

14. The refill head according to claim 12 wherein the elastomeric ring portion nests within an annular depression formed in an outer surface of the sleeve portion, an outer surface of the elastomeric ring portion being substantially flush with the outer surface of the sleeve portion.

15. The refill head according to claim 12 wherein the sleeve cavity comprises: an entry section having a first minimum diameter and comprising the open bottom end of the sleeve cavity; and an engagement section having a second minimum diameter that is less than the
first minimum diameter, an inner surface of the sleeve portion that defines the sleeve cavity comprising an annular transverse shoulder located between the entry section and the engagement section.

16. The refill head according to claim 15 wherein the engagement section of the sleeve cavity and the elastomeric ring portion are transversely aligned so that a transverse plane that is perpendicular to the longitudinal axis of the sleeve cavity intersects both the engagement section of the sleeve cavity and the elastomeric ring portion.

17. The refill head according to claim 15 wherein the sleeve cavity comprises an uppermost section located above the engagement section, the uppermost section having a transverse cross-sectional area that decreases with distance from the engagement section.

18. The refill head according to claim 12 wherein the elastomeric ring portion has a maximum thickness that is greater than a maximum thickness of the elastomeric pad portion.

19. The refill head according to claim 11 wherein the elastomeric tooth contact element extending from the front surface of the head portion is aligned with and has the same shape as one of the elastomeric protuberances extending from the rear surface of the pad portion.

* * * * *

UNITED STATES PATENT AND TRADEMARK OFFICE
CERTIFICATE OF CORRECTION

PATENT NO. : 10,500,023 B2
APPLICATION NO. : 15/361991
DATED : December 10, 2019
INVENTOR(S) : Takahide Okai It is certified that error appears in the above-identified patent and that said Letters Patent is hereby corrected as shown below:

On the Title Page

In item (73), after "New York, NY (US)", add "; and OMRON HEALTHCARE CO., LTD., Kyoto (JP).".

In the Specification

In Column 9, Line 19, after "edge of the", delete "the".

In Column 10, Line 49, after "113 and the", delete "the".

Signed and Sealed this
Twenty-fifth Day of February, 2020

Andrei Iancu
*Director of the United States Patent and Trademark Office*